(12) United States Patent
Lau

(10) Patent No.: US 12,161,839 B1
(45) Date of Patent: Dec. 10, 2024

(54) AUTOMATED FLUID INFUSION SYSTEM AND METHOD FOR MEDICAL APPLICATIONS

(71) Applicant: Gregory Lau, Butler, AL (US)

(72) Inventor: Gregory Lau, Butler, AL (US)

(73) Assignee: VLAB, LLC, Camden, DE (US)

( * ) Notice: Subject to any disclaimer, the term of this patent is extended or adjusted under 35 U.S.C. 154(b) by 506 days.

(21) Appl. No.: 17/585,086

(22) Filed: Jan. 26, 2022

Related U.S. Application Data

(60) Provisional application No. 63/141,684, filed on Jan. 26, 2021.

(51) Int. Cl.
*A61M 5/155* (2006.01)
*A61M 5/14* (2006.01)
*A61M 5/162* (2006.01)
*A61M 5/168* (2006.01)

(52) U.S. Cl.
CPC ............ *A61M 5/155* (2013.01); *A61M 5/162* (2013.01); *A61M 5/16813* (2013.01); *A61M 5/16881* (2013.01); *A61M 2005/1402* (2013.01); *A61M 2205/3331* (2013.01)

(58) Field of Classification Search
CPC .. A61M 5/155; A61M 5/162; A61M 5/16813; A61M 5/16881; A61M 2005/1402; A61M 2205/3331; A61M 5/1483; A61M 5/1486; A61M 25/10184
See application file for complete search history.

(56) References Cited

U.S. PATENT DOCUMENTS

| 4,048,994 A * | 9/1977 | Lo ............................ A61J 1/10 604/142 |
| 4,735,613 A | 4/1988 | Bellin et al. |
| 5,053,011 A | 10/1991 | Strobel et al. |
| 5,749,854 A * | 5/1998 | Shen ................... A61M 5/1486 604/141 |
| 9,345,830 B2 | 5/2016 | Miller |
| 2010/0204649 A1 * | 8/2010 | Miller ................... A61M 5/145 604/404 |
| 2011/0196304 A1 | 8/2011 | Kramer et al. |

* cited by examiner

*Primary Examiner* — Theodore J Stigell
(74) *Attorney, Agent, or Firm* — Schwartz Law Firm, P.C.

(57) ABSTRACT

An automated medical fluid infusion system for delivering a bio-compatible fluid to a patient. The bio-compatible fluid is contained in a collapsible IV fluid bag having a deliver port connected by a catheter to the patient. The medical fluid infusion system utilizes an inflatable pressure bag adapted for holding the IV bag and communicating via flexible tubing with a source of compressed gas. A pressure venting device is operatively connected to the flexible tubing and resides between the pressure bag and the source of compressed gas. The pressure venting device includes a housing, a movable bleed screw located within the housing, and a chamfered bleed port. The bleed screw has a tapered end configured to selectively engage the housing at the chamfered bleed port, thereby adjustably opening and closing the bleed port to control the flow of compressed gas through the flexible tubing to the pressure bag.

20 Claims, 8 Drawing Sheets

AUTOMATED FLUID INFUSION SYSTEM AND METHOD FOR MEDICAL APPLICATIONS

TECHNICAL FIELD AND BACKGROUND OF THE DISCLOSURE

The present disclosure relates broadly and generally to an automated fluid infusion system and method for medical applications. The invention functions to increase the delivery of bio-compatible fluids to medical patients. Embodiments of the invention are especially applicable for use in hospitals, mobile hospitals, emergency rooms, urgent care facilities, ambulances and other emergency response vehicles, military medical response vehicles and onsite triage tents.

The flow of fluids delivered from a standard collapsible IV fluid bag through an IV catheter can be represented by the following formula:

$$\text{Flow} = \frac{\pi * \text{Pressure} * \text{radius}^4}{8 * \text{viscosity} * \text{length of tubing}}$$

As indicated above, the pressure gradient is an important factor in determining how quickly fluid can be delivered to the patient. As such, pressure bags are commonly used in the medical field to speed the infusion of fluids. As the time to deliver a fluid bolus via pressure bag can vary widely, effective administration and monitoring is critically important to ensure proper fluid volume management, control and any necessary adjustment. Too little or too much fluid at critical times can increase patient morbidity and cause death.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an automated medical fluid infusion system for delivering a bio-compatible fluid to a patient. The bio-compatible fluid is contained in a collapsible IV fluid bag having a deliver port connected by a catheter to the patient. The medical fluid infusion system comprises an inflatable pressure bag adapted for holding the IV bag and communicating via flexible tubing with a source of compressed gas. A pressure venting device is operatively connected to the flexible tubing and resides between the pressure bag and the source of compressed gas. The pressure venting device comprises a housing, a movable bleed screw located within the housing, and a chamfered bleed port. The bleed screw has a tapered end configured to selectively engage the housing at the chamfered bleed port, thereby adjustably opening and closing the bleed port to control the flow of compressed gas through the flexible tubing to the pressure bag. As used herein, the term "automated" refers to the use of one or more airflow management devices (discussed further below) to automatically maintain a substantially constant prescribed pressure inside the inflatable pressure bag throughout the entire discharge of fluid from the IV fluid bag.

According to another exemplary embodiment, a manual vent control knob is configured for selectively moving the bleed screw between open and closed positions within the housing.

According to another exemplary embodiment, the bleed screw extends across an inline gas flow path defined by flexible tubing.

According to another exemplary embodiment, the bleed port is laterally offset from the inline gas flow path.

According to another exemplary embodiment, the bleed port has a chamfer angle of between 30 and 60 degrees.

According to another exemplary embodiment, the tapered end of the bleed screw is tapered at an angle corresponding to the chamfer angle of the bleed port.

According to another exemplary embodiment, a pressure measurement device is operatively connected to the flexible tubing and resides between the pressure venting device and the pressure bag. The pressure measurement device (e.g., manometer) includes a housing, a movable spring-biased scale rod located within the housing, and a gas inlet proximate a base of the scale rod. Gas flow through the flexible tubing enters the housing through the gas inlet and urges the scale rod outwardly from the housing against a spring biasing force (e.g., created by a calibrated compression spring), thereby indicating a degree of gas pressure inside the pressure bag. The manometer automatically vents the system when pressure inside the pressure bag exceeds a prescribed threshold, thereby automatically maintaining bag pressure at a substantially consistent fixed pressure throughout the delivery of IV fluid to the patient.

According to another exemplary embodiment, the pressure bag is configured to apply substantially uniform pressure to the IV bag within a range of between 200-400 mm Hg.

In another exemplary embodiment, the present disclosure comprises an automated medical fluid infusion system for delivering a bio-compatible fluid to a patient. The bio-compatible fluid is contained in a collapsible IV fluid bag having a deliver port connected by a catheter to the patient. The medical fluid infusion system comprises an inflatable pressure bag adapted for holding the IV bag and communicating via flexible tubing with a source of compressed gas. A rapid inflate device is operatively connected to the flexible tubing and resides between the pressure bag and the source of compressed gas. The rapid inflate device include a housing, a movable spring-loaded push toggle located within the housing, and a rapid-rate annular flow port. The spring-loaded toggle has a port-sealing end configured to selectively engage the housing at the rapid-rate flow port, thereby selectively opening and closing the rapid-rate flow port to control the flow of compressed gas through the flexible tubing to the pressure bag.

According to another exemplary embodiment, the rapid inflate device comprises a manual push button located outside of the housing and connected to the spring-loaded push toggle.

According to another exemplary embodiment, a gas flow control device is operatively connected to the flexible tubing and resides between the pressure bag and the source of compressed gas. The gas flow control device includes a housing, a movable valve finger located within the housing, and an annular working-rate flow port. The valve finger is configured to selectively engage the housing at the working-rate flow port, thereby selectively opening and closing the working-rate flow port to control the flow of compressed gas through the flexible tubing to the pressure bag.

According to another exemplary embodiment, and comprising a gas flow indicator proximate the gas flow control device and configured to indicate a flow of gas from the source of compressed gas.

According to another exemplary embodiment, the gas flow indicator comprises a mechanical gas gauge.

According to another exemplary embodiment, the mechanical gas gauge includes a transparent hollow column and a ball float inside the column.

BRIEF DESCRIPTION OF THE DRAWINGS

Exemplary embodiments of the present disclosure will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
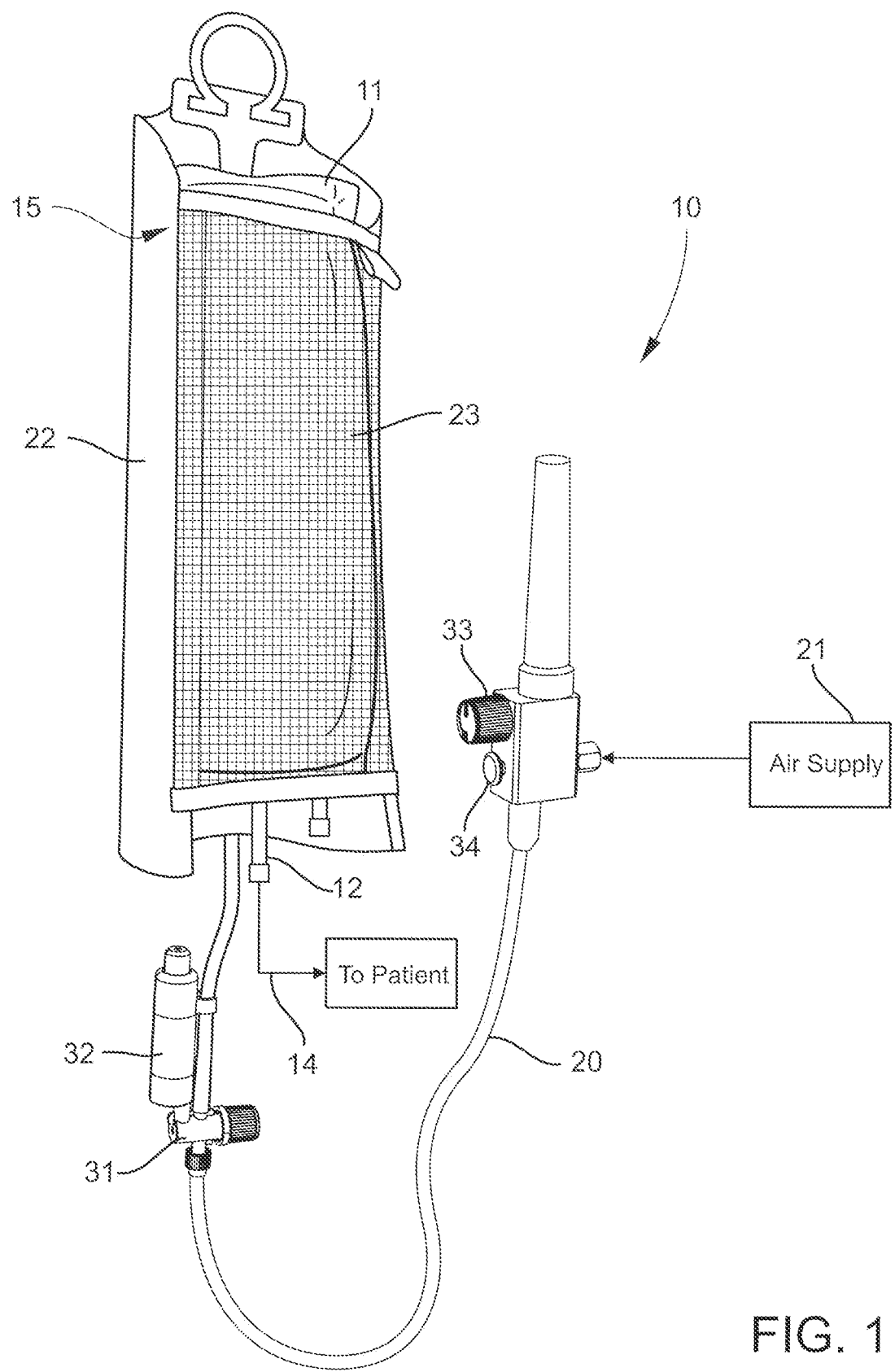
FIGS. 1 and 2 are views illustrating exemplary components of the present medical fluid infusion system and method.
Figure 2:
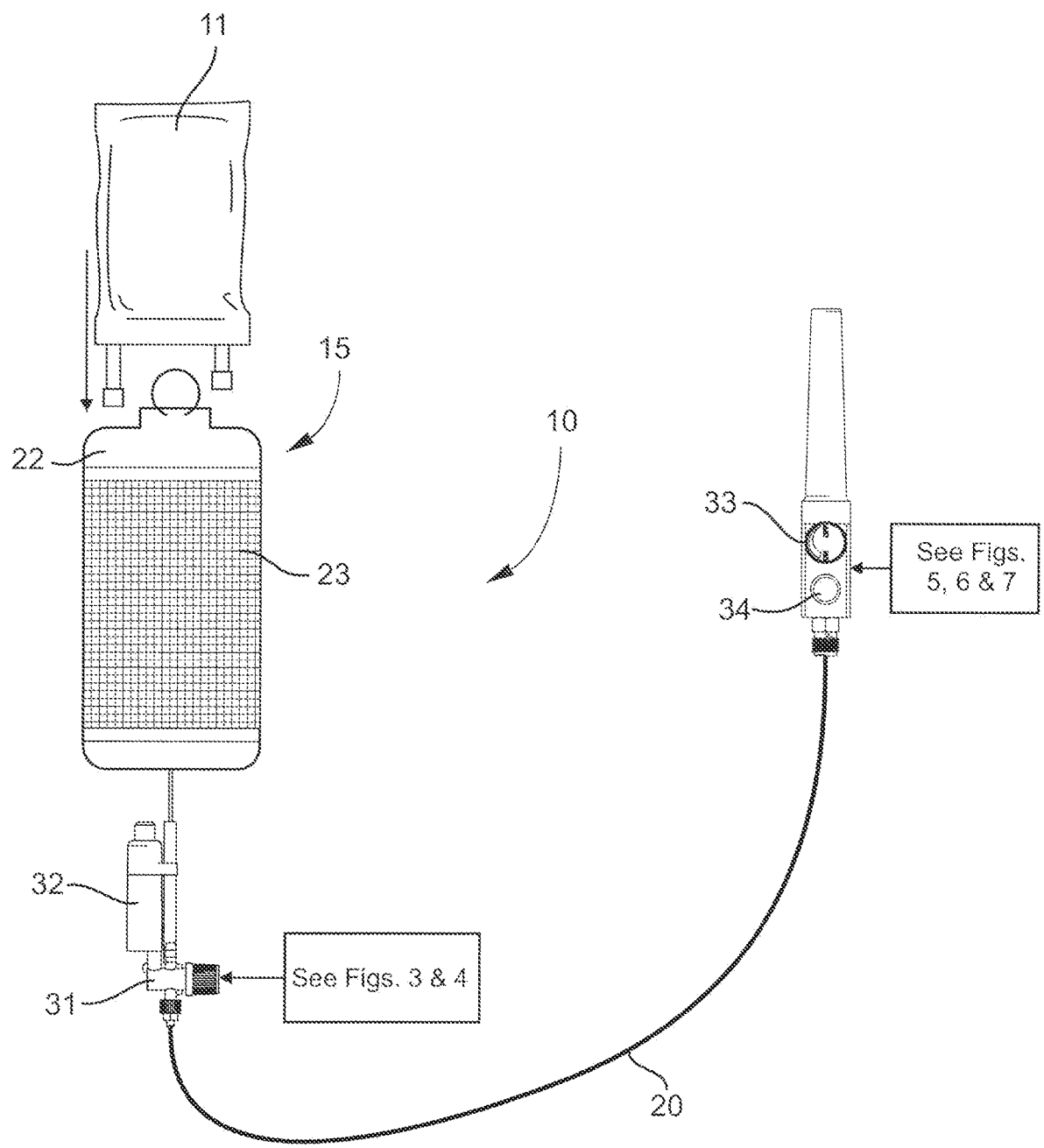

Referring now specifically to the drawings, an automated medical fluid infusion system according to one exemplary embodiment of the present disclosure is illustrated in FIGS. 1 and 2, and shown generally at broad reference numeral 10. As described further below, the exemplary infusion system utilizes pressurization to rapidly deliver a bio-compatible fluid to a medical patient. The bio-compatible fluid is contained in a standard collapsible IV fluid bag 11 having a deliver port 12 connected by a catheter 14 to the patient.

As shown in FIGS. 1 and 2, the exemplary system incorporates an inflatable pressure bag 15 communicating through one or more lengths of flexible medical tubing 20 with a source of compressed air 21 (or other non-flammable gas), and one or more of the present airflow management devices discussed below. The pressure bag 15 has an inflatable bladder 22 and see-through fabric mesh panel 23 sewn along opposing side edges to the bladder 22, and defining an open top for receiving the IV fluid bag 11. The IV fluid bag 11 is securely held between the bladder 22 and mesh panel 23 such that increased pressure created by the inflating bladder 22 exerts substantially continuous and uniform pressure on the IV fluid bag 11 during use. The airflow management devices of the present system comprise a pressure venting device 31, a pressure measurement device 32 (e.g., manometer), an airflow control device 33, and a rapid inflate device 34. Each of these devices is discussed separately below.

Figure 3:
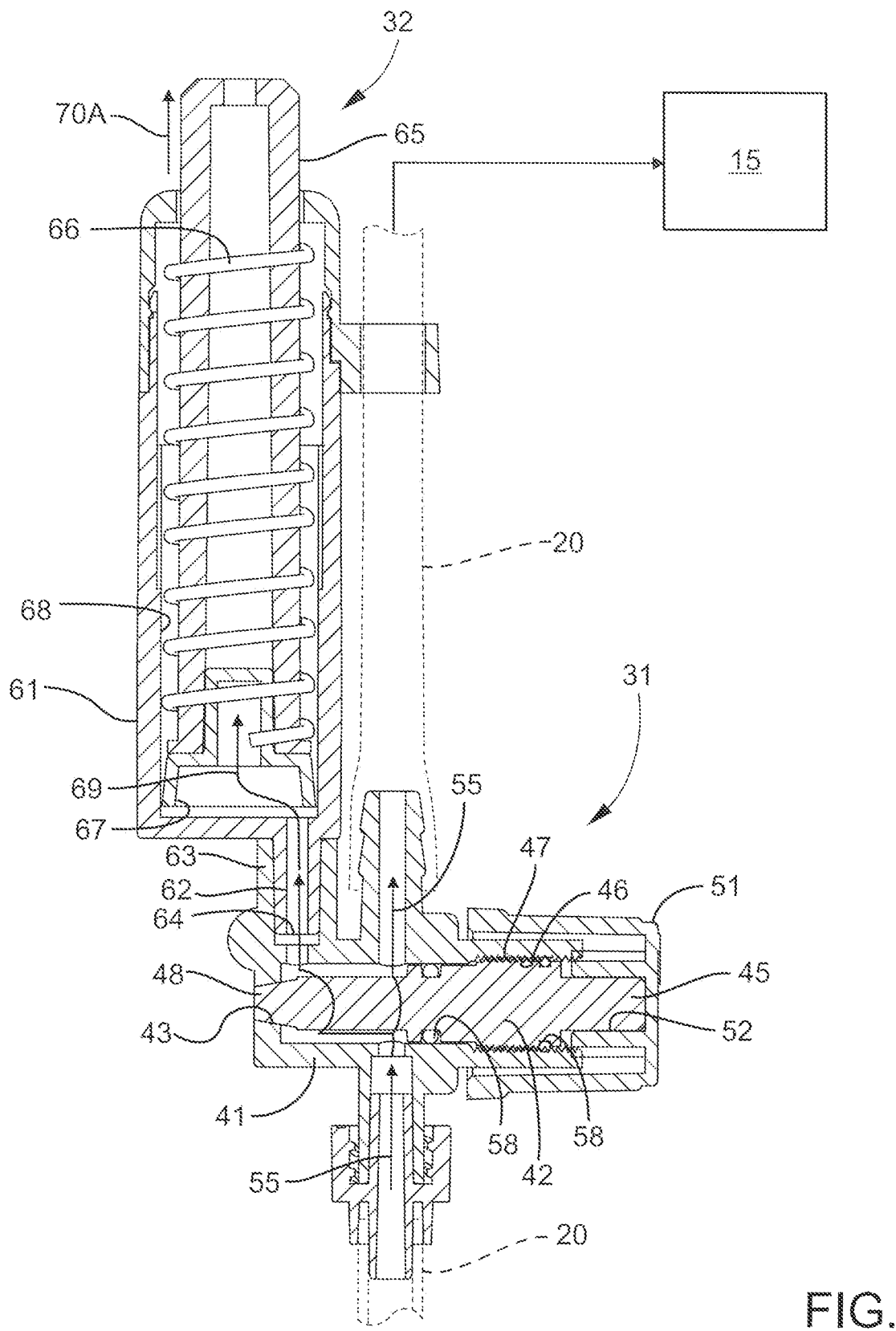
FIGS. 3 and 4 are cross-sectional views of the pressure venting device and a pressure measurement device incorporated in the exemplary medical fluid infusion system and method.
Figure 4:
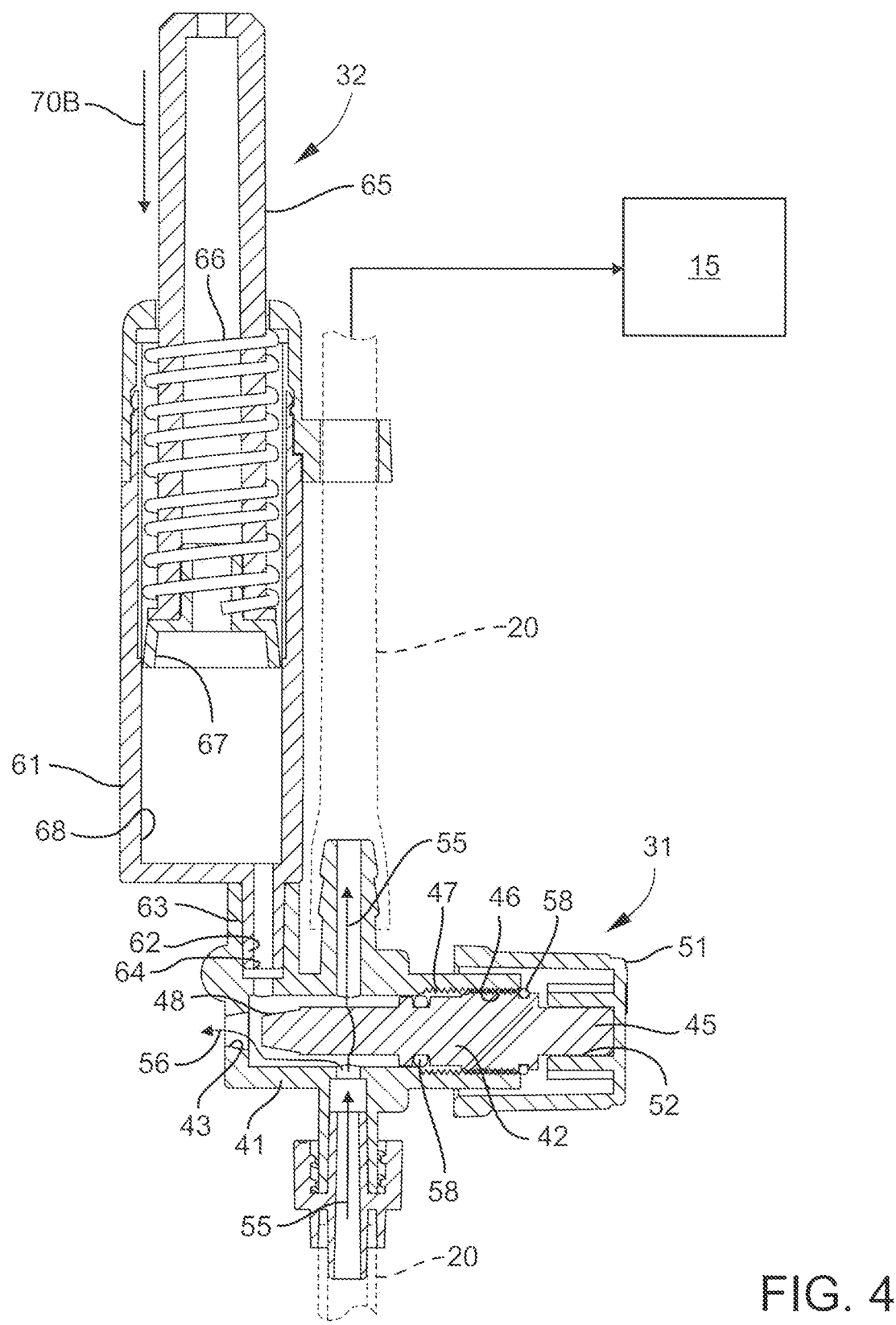

Referring to FIGS. 2, 3 and 4, the exemplary pressure venting device 31 is operatively or "fluidly" connected to the medical tubing 20 and resides between the pressure bag 15 and the source of compressed air 21. The pressure venting device 31 includes a sealed housing 41, a movable bleed screw 42 located within the housing 41, and a chamfered bleed port 43. The bleed screw 42 has a square head 45, a threaded neck portion 46 adjacent the head 45 and configured to mate with a complementary internal thread 47 of the housing 41, and a tapered (or frustoconical) distal end 48.

The frustoconical distal end 48 is configured to selectively engage the housing 41 at the annular chamfered bleed port 43. A vent control knob 51 defines an internal square socket 52 which receives the square head 45 of the bleed screw 42, and when manually rotated clockwise and counterclockwise functions to move the bleed screw 42 linearly between open and closed positions within the housing 41. The bleed screw 42 extends across the airflow path defined by aligned ends of the medical tubing 20, and has a sufficiently small intermediate diameter to permit inline passage of airflow around the bleed screw 42 and through the housing 41. See direction arrow 55 in FIGS. 3 and 4. In exemplary embodiments, the bleed port 43 is laterally offset from the inline flow path defined by the medical tubing 20.

When in the closed position shown in FIG. 3, the frustoconical distal end 48 of the bleed screw 42 closely engages the housing 41 at the complementary chamfered bleed port 43. This directs substantially 100% of the airflow entering the housing 41 downstream through the medical tubing 20 to continuously pressurize the inflatable bladder 22 of pressure bag 15. When the bleed screw 42 is in a fully open position shown in FIG. 4, a portion of airflow entering the housing 41 is allowed to escape (or vent) through the bleed port 43—as indicated by direction arrow 56. By manually rotating the control knob 51, the frustoconical distal end 48 of the bleed screw 42 moves relative to the chamfered bleed port 43, thereby adjusting a relative size of the exhaust air passage in the housing 41. This allows for an adjusted degree of venting such that air pressure within the pressure bag 15 is precisely set during delivery of IV fluid to the patient. In exemplary embodiments, the distal end 48 of the bleed screw 42 and chamfered bleed port 43 have complementary cross-sectional angles of between 30-60 degrees. One or more O-rings 58 may be provided on the movable bleed screw 42 to seal spaces between the screw 42 and housing 41.

The pressure measurement device 32 is also operatively fluidly connected to the medical tubing 20 and resides between the pressure venting device 31 and the pressure bag 15. In the present embodiment, the pressure measurement device 32 includes a housing 61 which is integrally joined to the housing 41 of the pressure venting device 31 at respective complementary male and female connectors 62, 63. The male connector 62 of housing 61 defines an air inlet 64 which allows passage of compressed air between the devices 31, 32. See flow arrow 69 in FIG. 3. In the pressure measurement device 32, a vertical scaled rod 65 is surrounded by a calibrated compression spring 66 inside the housing 61 and comprises a closed base 67 substantially sealed against interior walls 68 of the housing 61. Air entering the housing 61 through the inlet 64 urges the base 67 and scaled rod 65 upwardly as indicated by direction arrow 70A against the biasing force of the calibrated spring 66. The relative degree of pressure inside the device 32 determines the extent to which the scaled rod 65 projects outwardly from a top of the housing 61. This pressure is readily measured using graduated visual markings on the scaled rod 65. A maximum degree of pressure is supplied to the pressure bag 15 when the bleed screw 42 is fully closed, as described above and shown in FIG. 3. Bag pressure is selectively adjusted down or lowered by manually rotating the vent control knob 51 to unseat the bleed screw 42 from sealing engagement with the housing 41 at the bleed port 43. When the bleed port 43 is fully open, as shown in FIG. 4, the scaled rod 65 retracts inside the housing 61 as indicated by direction arrow 70B—the exposed visual markings on the lowered rod 65 indicating a reduced bag pressure. In the exemplary embodiment, the calibrated spring 66 is fabricated such that when bag pressure exceeds a predetermined threshold (e.g., 300 mm Hg) the base 67 of scaled rod 65 extends to a vent point inside the manometer housing 61. At the vent point, air inside the housing 61 is automatically exhausted in a conventional manner common in prior art manometers used in the industry. This automatic venting maintains pressure inside pressure bag 15 at the prescribed pressure level—e.g., 300 mmHg. As discussed above, adjustably opening the bleed port 43 reduces the fixed bag pressure to a lesser amount, a fixed pressure less than 300 mmHg. In alternative embodiments, the spring 66 may be calibrated to automatically vent the manometer housing 61 at higher threshold bag pressures ranging from 300 to 600 mmHg.

Figure 5:
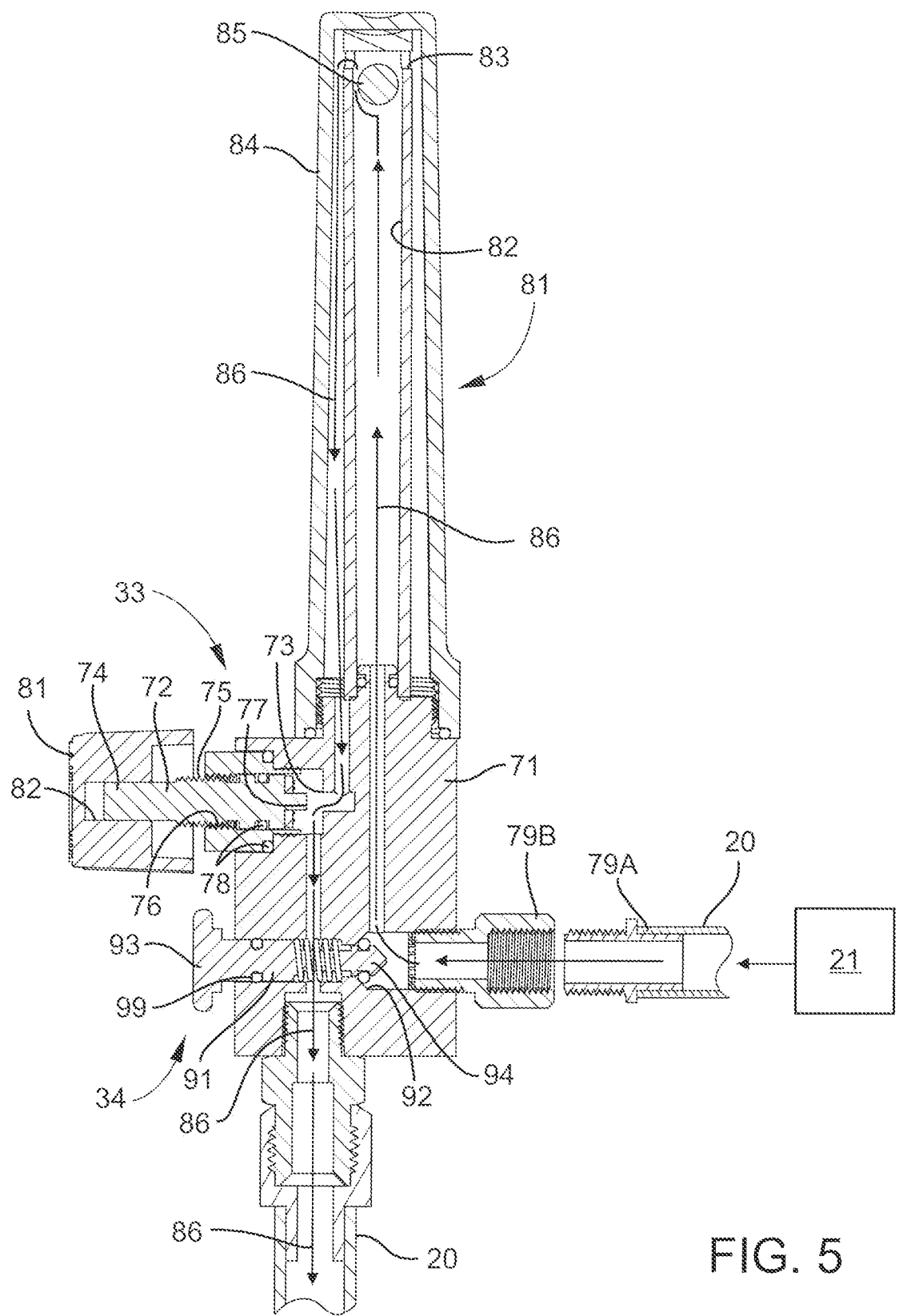
FIGS. 5, 6, and 7 are cross-sectional views of the airflow control device and a rapid inflate device incorporated in the exemplary medical fluid infusion system and method.
Figure 6:
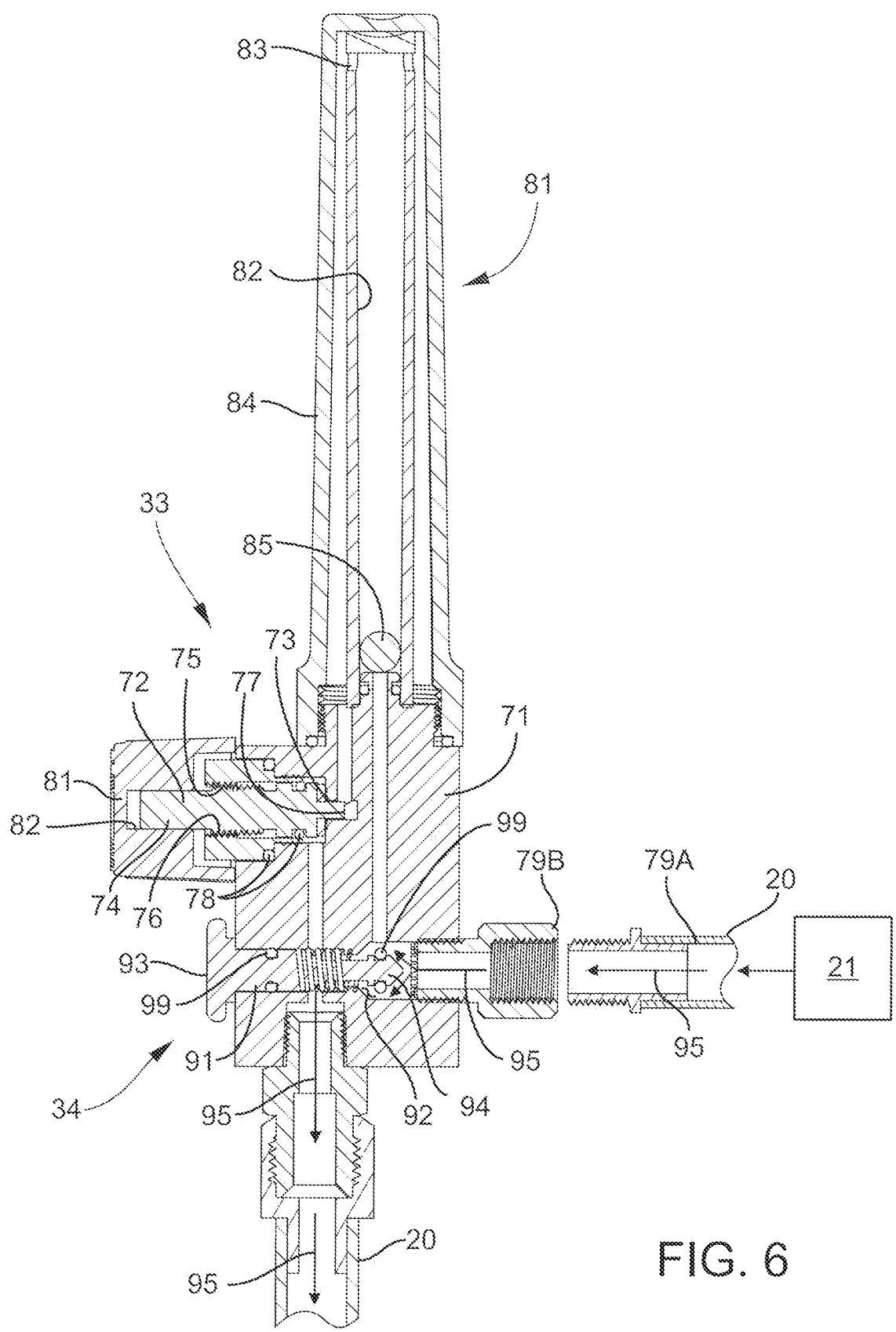
Figure 7:
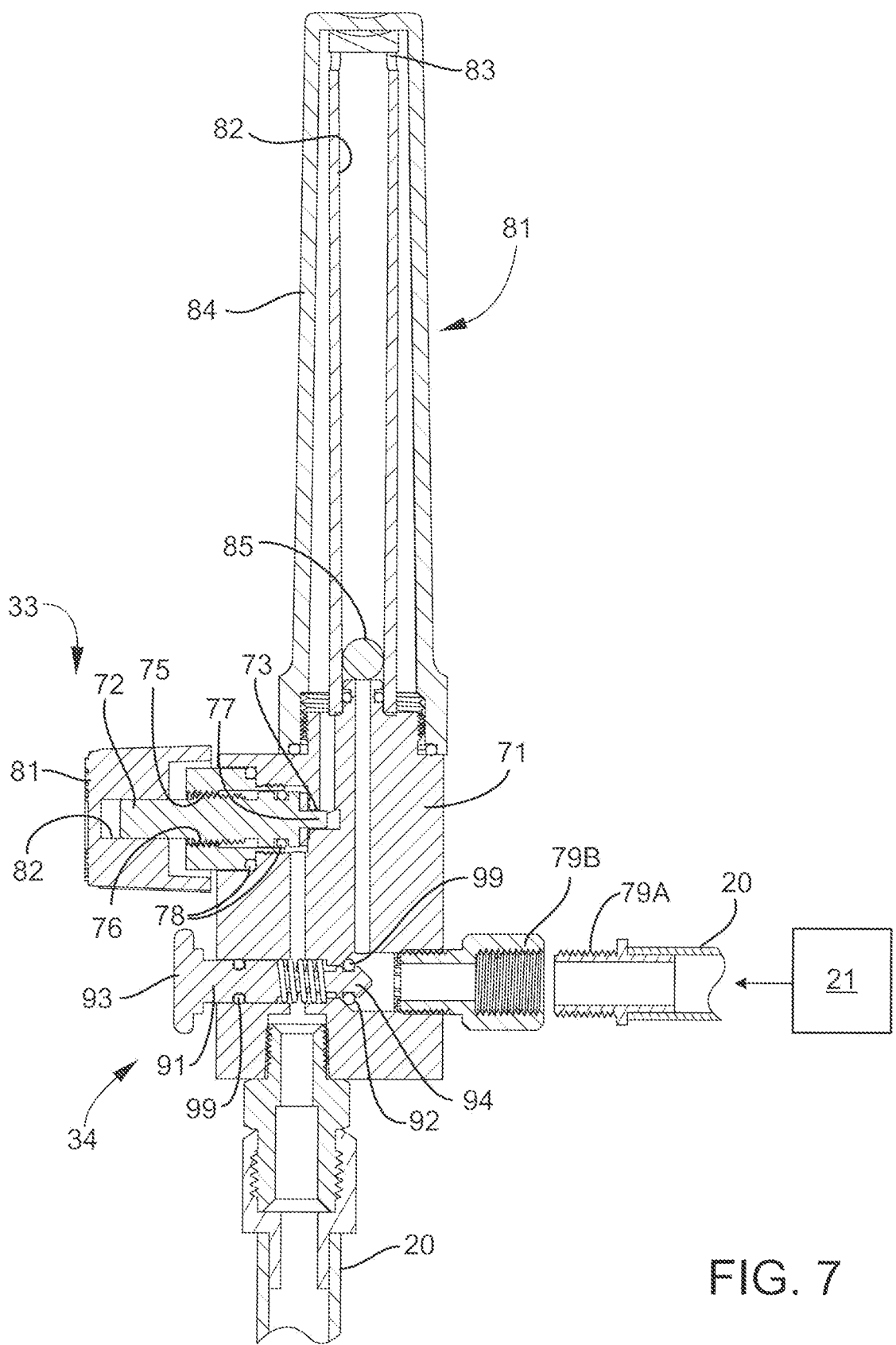

The airflow control device 33 and rapid inflate device 34 are shown in FIGS. 5, 6 and 7, and are likewise operatively fluidly connected to the medical tubing 20 between the pressure bag 15 and the source of compressed air 21. The devices 33, 34 may be integrally formed together as a single unit as shown, or separately formed and attached to the medical tubing 20 at spaced or adjacent locations.

The exemplary airflow control device 33 includes a sealed housing 71, a movable valve finger 72 located within the housing 71, and a working-rate flow port 73. The valve finger 72 has a square head 74, a threaded body portion 75 adjacent the head 74 and configured to mate with a complementary internal thread 76 of the housing 71, and a reduced diameter seal tip 77 configured to selectively engage the housing 71 at the working-rate flow port 73. An airflow control dial 81 defines an internal square socket 82 which receives the square head 74 of the threaded valve finger 72, and when manually rotated clockwise or counterclockwise functions to move the seal tip 77 of the finger 72 between open and closed positions within the housing 71. One or more O-rings 78 may be used to seal spaces between components of the valve finger 72 and housing 71.

The source of compressed air 21 connects to the housing 71 of airflow control device 33 via complementary threaded male and female connectors 79A, 79B. Compressed air enters the housing 71 and is directed into and through an airflow indicator 81. The exemplary airflow indicator 81 comprises a mechanical gauge incorporating a transparent interior column 82 sealed at its base to the housing 71, and having air ports 83 formed at its top end. A larger transparent columnar shield 84 surrounds the interior column 82 and is likewise sealed at its base to the housing 71. As compressed air enters the interior column 82 of the indicator 81 and flows through the housing 71, a ball float 85 elevates inside the column 82—as shown in FIG. 5. The air passes through the open working-rate flow port 73 and through the housing 71 as indicated by flow arrows 86. In the open position, the working-rate flow port 73 directs compressed air through the medical tubing 20 to the pressure bag 15—inflating the air bladder 22 to apply substantially uniform pressure to the IV fluid bag 11 within a range of between 200-400 mm Hg, and preferably about 300 mm Hg (+/−15%). The working flow rate of compressed air passing through the open airflow control device 33, through the medical tubing 20, and into the pressure bag 15 is fixed within a range of 2-5 liters/min.

In the exemplary embodiment, the rapid inflate device 34 is integrated in the sealed housing 71, and comprises a movable spring-loaded push toggle 91 and a rapid-rate flow port 92. The spring-loaded toggle 91 has an annular push button 93 located outside of the housing 71 and a port-sealing end 94. The port-sealing end 94 is configured to selectively engage the housing 71 at the rapid-rate flow port 92, thereby selectively opening and closing the rapid-rate flow port 92 to control the flow of compressed air through the medical tubing 20 to the pressure bag 15. One or more O-rings 99 may be used to seal spaces between components of the push toggle 91 and housing 71.

Compressed air entering the housing 71 extends along one or both of two available airflow paths depending upon the open/closed condition of the airflow control device 33 and the selected position of the spring-loaded toggle 91. When the airflow control device 33 is open and the rapid-rate flow port 92 closed, as shown in FIG. 5, compressed air passes through the housing 71 as indicated by flow arrows 86 mentioned above. When the airflow control device 33 is closed and the spring-loaded toggle 91 is manually depressed as shown in FIG. 6, compressed air bypasses the airflow indicator 81 and passes directly through the rapid-rate flow port 92 and into medical tubing 20, as indicated by flow arrows 95. In a third scenario (not shown), the spring-loaded toggle 91 may be manually pressed to open the rapid-rate flow port 92, while the airflow control device 33 is also in the open position. FIG. 7 shows both the airflow control device 33 and the rapid inflate device 34 in closed conditions. In this scenario, airflow through the medical tubing 20 is entirely shutoff.

Figure 8:
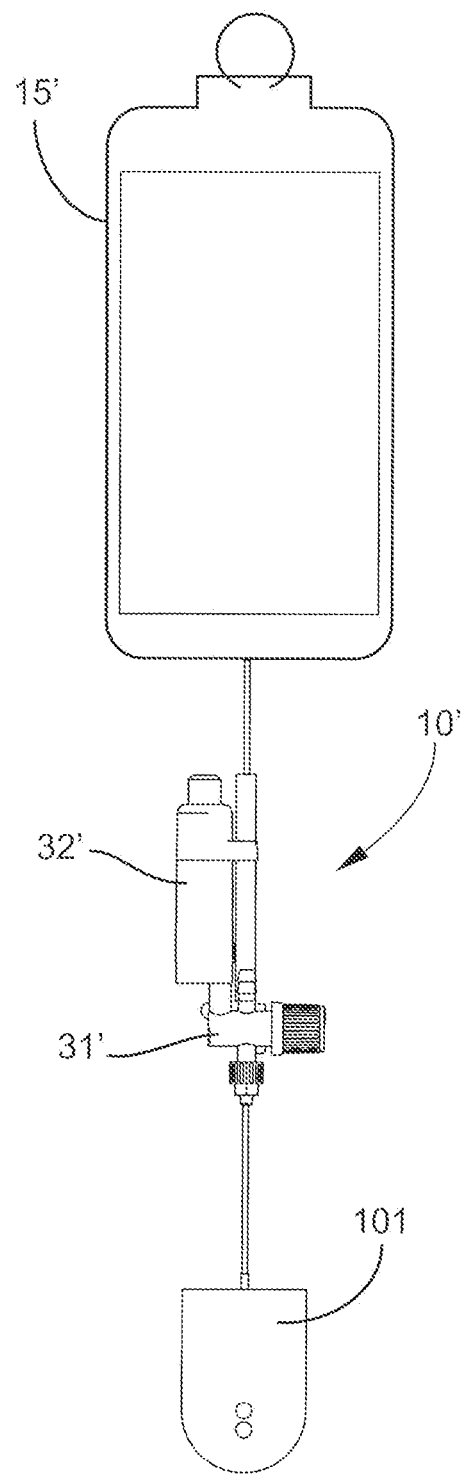
FIGS. 8 and 9 illustrate alternative embodiments of the present disclosure.
Figure 9:
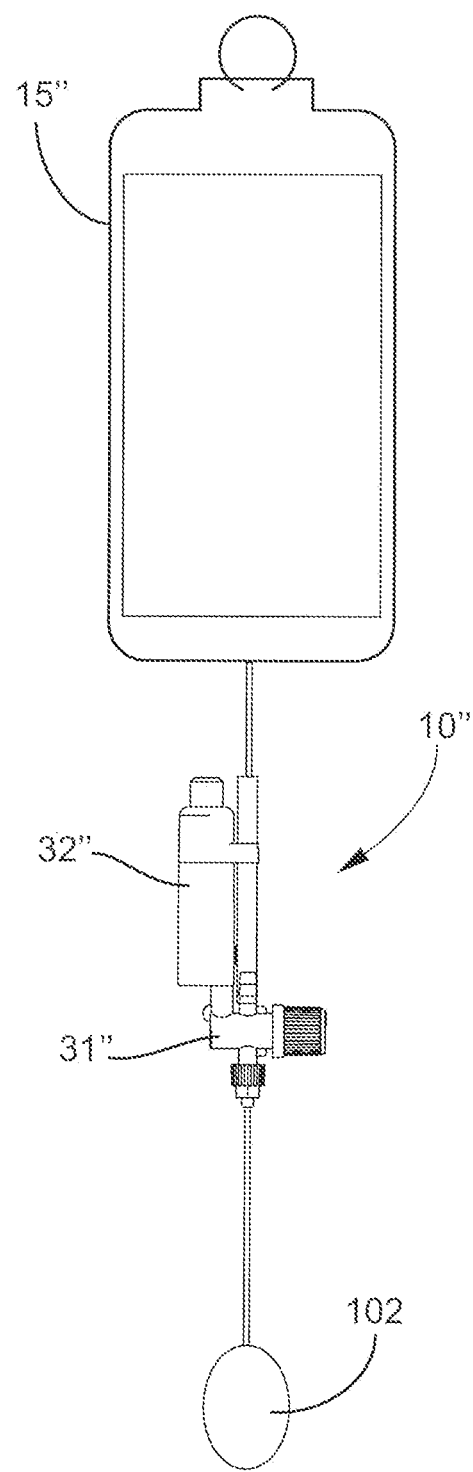

In alternative embodiments shown in FIGS. 8 and 9, the exemplary medical fluid infusion system 10', 10" may comprise a pressure bag 15', 15" utilized in combination with an electronic DC air pump 101, as shown in FIG. 8, or manual air pump 102, as shown in FIG. 9. In either alternative embodiment 10' or 10", the exemplary system may incorporate any one or more of the airflow management devices described above including, for example, the pressure venting device 31', 31" and pressure measurement device 32', 32".

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112 (f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. An automated medical fluid infusion system for delivering a bio-compatible fluid to a patient, the bio-compatible fluid being contained in a collapsible IV fluid bag having a deliver port connected by a catheter to the patient, said medical fluid infusion system comprising:
    an inflatable pressure bag adapted for holding the IV fluid bag and communicating via flexible tubing with a source of compressed gas; and
    a pressure venting device operatively connected to said flexible tubing and residing between said pressure bag and the source of compressed gas, and wherein said pressure venting device comprises a housing, a movable bleed screw located within said housing, and a chamfered bleed port, and said bleed screw having a tapered end configured to selectively engage said housing at said chamfered bleed port, thereby adjustably opening and closing said bleed port to control the flow of compressed gas through the flexible tubing to said pressure bag.

2. The medical fluid infusion system according to claim 1, and comprising a manual vent control knob for selectively moving said bleed screw between open and closed positions within said housing.

3. The medical fluid infusion system according to claim 1, wherein said bleed screw extends across a gas flow path defined by said flexible tubing.

4. The medical fluid infusion system according to claim 3, wherein said bleed port is laterally offset from said gas flow path.

5. The medical fluid infusion system according to claim 4, wherein said bleed port has a chamfer angle of between 30 and 60 degrees.

6. The medical fluid infusion system according to claim 5, wherein said tapered end of said bleed screw is tapered at an angle corresponding to said chamfer angle of said bleed port.

7. The medical fluid infusion system according to claim 1, and comprising a pressure measurement device operatively connected to said flexible tubing and residing between said pressure venting device and said pressure bag, and wherein said pressure measurement device comprises a housing, a movable spring-biased scale rod located within said housing, and a gas inlet proximate a base of said scale rod, whereby gas flow through said flexible tubing enters said housing through said gas inlet and urges said scale rod outwardly from said housing against a spring biasing force, thereby indicating a degree of gas pressure inside said pressure bag.

8. The medical fluid infusion system according to claim 1, wherein said pressure bag is configured to apply substantially uniform pressure to the IV fluid bag within a range of between 200-400 mm Hg.

9. An automated medical fluid infusion system for delivering a bio-compatible fluid to a patient, the bio-compatible fluid being contained in a collapsible IV fluid bag having a deliver port connected by a catheter to the patient, said medical fluid infusion system comprising:
    an inflatable pressure bag adapted for holding the IV fluid bag and communicating via flexible tubing with a source of compressed gas; and
    a rapid inflate device operatively connected to said flexible tubing and residing between said pressure bag and the source of compressed gas, and wherein said rapid inflate device comprises a housing, a movable spring-loaded push toggle located within said housing, and a rapid-rate flow port, and said spring-loaded push toggle having a port-sealing end configured to selectively engage said housing at said rapid-rate flow port, thereby selectively opening and closing said rapid-rate flow port to control the flow of compressed gas through the flexible tubing to said pressure bag.

10. The medical fluid infusion system according to claim 9, wherein said rapid inflate device comprises a manual push button located outside of said housing and connected to said spring-loaded push toggle.

11. The medical fluid infusion system according to claim 9, and comprising a gas flow control device operatively connected to said flexible tubing and residing between said pressure bag and the source of compressed gas, and wherein said gas flow control device comprises a housing, a movable valve finger located within said housing, and a working-rate flow port, whereby said valve finger is configured to selectively engage said housing at said working-rate flow port, thereby selectively opening and closing said working-rate flow port to control the flow of compressed gas through the flexible tubing to said pressure bag.

12. The medical fluid infusion system according to claim 11, and comprising a gas flow indicator proximate said gas flow control device and configured to indicate a flow of gas from the source of compressed gas.

13. The medical fluid infusion system according to claim 12, wherein said gas flow indicator comprises a mechanical gas gauge.

14. The medical fluid infusion system according to claim 13, wherein said mechanical gas gauge comprises a transparent hollow column and a ball float inside said column.

15. An automated medical fluid infusion system for delivering a bio-compatible fluid to a patient, the bio-compatible fluid being contained in a collapsible IV fluid bag having a deliver port connected by a catheter to the patient, said medical fluid infusion system comprising:
an inflatable pressure bag adapted for holding the IV fluid bag and communicating via flexible tubing with a source of compressed gas;
a pressure venting device operatively connected to said flexible tubing and residing between said pressure bag and the source of compressed gas, and wherein said pressure venting device comprises a housing, a movable bleed screw located within said housing, and a chamfered bleed port, and said bleed screw having a tapered end configured to selectively engage said housing at said chamfered bleed port, thereby adjustably opening and closing said bleed port to control the flow of compressed gas through the flexible tubing to said pressure bag; and
a rapid inflate device operatively connected to said flexible tubing and residing between said pressure bag and the source of compressed gas, and wherein said rapid inflate device comprises a housing, a movable spring-loaded push toggle located within said housing, and a rapid-rate flow port, and said spring-loaded push toggle having a port-sealing end configured to selectively engage said housing at said rapid-rate flow port, thereby selectively opening and closing said rapid-rate flow port to control the flow of compressed gas through the flexible tubing to said pressure bag.

16. The medical fluid infusion system according to claim 15, wherein said tapered end of said bleed screw is tapered at an angle corresponding to a chamfer angle of said bleed port.

17. The medical fluid infusion system according to claim 15, and comprising a pressure measurement device operatively connected to said flexible tubing and residing between said pressure venting device and said pressure bag, and wherein said pressure measurement device comprises a housing, a movable spring-biased scale rod located within said housing, and a gas inlet proximate a base of said scale rod, whereby gas flow through said flexible tubing enters said housing through said gas inlet and urges said scale rod outwardly from said housing against a spring biasing force, thereby indicating a degree of gas pressure inside said pressure bag.

18. The medical fluid infusion system according to claim 15, wherein said rapid inflate device comprises a manual push button located outside of said housing and connected to said spring-loaded push toggle.

19. The medical fluid infusion system according to claim 15, and comprising a gas flow control device operatively connected to said flexible tubing and residing between said pressure bag and the source of compressed gas, and wherein said gas flow control device comprises a housing, a movable valve finger located within said housing, and a working-rate flow port, whereby said valve finger is configured to selectively engage said housing at said working-rate flow port, thereby selectively opening and closing said working-rate flow port to control the flow of compressed gas through the flexible tubing to said pressure bag.

20. An automated medical fluid infusion system for delivering a bio-compatible fluid to a patient, the bio-compatible fluid being contained in a collapsible IV fluid bag having a deliver port connected by a catheter to the patient, said medical fluid infusion system comprising:
an inflatable pressure bag adapted for holding the IV fluid bag and communicating via flexible tubing with a source of compressed gas;
a pressure venting device operatively connected to said flexible tubing and residing between said pressure bag and the source of compressed gas, and wherein said pressure venting device comprises a housing, a movable bleed screw located within said housing, and a chamfered bleed port, and said bleed screw having a tapered end configured to selectively engage said housing at said chamfered bleed port, thereby adjustably opening and closing said bleed port to control the flow of compressed gas through the flexible tubing to said pressure bag;
a pressure measurement device operatively connected to said flexible tubing and residing between said pressure venting device and said pressure bag, and wherein said pressure measurement device comprises a housing, a movable spring-biased scale rod located within said housing, and a gas inlet proximate a base of said scale rod, whereby gas flow through said flexible tubing enters said housing through said gas inlet and urges said scale rod outwardly from said housing against a spring biasing force, thereby indicating a degree of gas pressure inside said pressure bag;
a rapid inflate device operatively connected to said flexible tubing and residing between said pressure bag and the source of compressed gas, and wherein said rapid inflate device comprises a housing, a movable spring-loaded push toggle located within said housing, and a rapid-rate flow port, and said spring-loaded push toggle having a port-sealing end configured to selectively engage said housing at said rapid-rate flow port, thereby selectively opening and closing said rapid-rate flow port to control the flow of compressed gas through the flexible tubing to said pressure bag;

a gas flow control device operatively connected to said flexible tubing and residing between said pressure bag and the source of compressed gas, and wherein said gas flow control device comprises a housing, a movable valve finger located within said housing, and a working-rate flow port, whereby said valve finger is configured to selectively engage said housing at said working-rate flow port, thereby selectively opening and closing said working-rate flow port to control the flow of compressed gas through the flexible tubing to said pressure bag; and a gas flow indicator proximate said gas flow control device and configured to indicate a flow of gas from the source of compressed gas.

\* \* \* \* \*